United States Patent [19]

Brandstetter et al.

[11] Patent Number: 5,008,851

[45] Date of Patent: Apr. 16, 1991

[54] OPTICAL HETERODYNING SYSTEM AND METHOD FOR RAPID OPTICAL PHASE AND AMPLITUDE MEASUREMENTS

[75] Inventors: Robert W. Brandstetter, Levittown; Benjamin J. Pernick, Forest Hills; Nils J. Fonneland, Lake Ronkonkoma; Stephen J. Caputi, Centerport, all of N.Y.

[73] Assignee: Grumman Aerospace Corporation, Bethpage, N.Y.

[21] Appl. No.: 328,637

[22] Filed: Mar. 27, 1989

[51] Int. Cl.$^5$ .................. G06G 7/00; G02F 1/11; G01B 9/02

[52] U.S. Cl. .................. 364/807; 350/358; 356/349

[58] Field of Search ............. 364/807, 822, 837, 821, 364/819, 827; 350/162.11, 162.12, 162.14, 371, 358; 356/349, 343; 324/77

[56] References Cited

U.S. PATENT DOCUMENTS

| | | | |
|---|---|---|---|
| 3,544,795 | 12/1970 | Korpel | 250/199 |
| 3,944,948 | 3/1976 | Redman et al. | 332/7.51 |
| 3,962,657 | 6/1976 | Redman et al. | 332/7.51 |
| 3,988,671 | 10/1976 | Pedinoff | 350/371 |
| 4,012,120 | 3/1977 | Kasiwada et al. | 364/827 |
| 4,097,110 | 6/1978 | Carey | 350/149 |
| 4,210,400 | 7/1980 | Misek | 356/359 |
| 4,295,741 | 10/1981 | Palma et al. | 356/349 |
| 4,365,310 | 12/1982 | Green | 364/822 |
| 4,448,494 | 5/1984 | Freyre | 350/358 |
| 4,460,250 | 7/1984 | Freyre et al. | 350/358 |
| 4,522,466 | 6/1985 | Lindig et al. | 350/162.12 |
| 4,644,267 | 2/1987 | Tsvi et al. | 350/358 |
| 4,645,300 | 2/1987 | Brandstetter et al. | 350/162.12 |
| 4,696,061 | 9/1987 | Labrum | 364/822 |
| 4,699,466 | 10/1987 | Brandstetter et al. | 350/162.12 |
| 4,771,397 | 9/1988 | Brandstetter et al. | 364/807 |
| 4,771,398 | 9/1988 | Brandstetter et al. | 364/807 |

Primary Examiner—Clark A. Jablon
Assistant Examiner—Jim Trammell
Attorney, Agent, or Firm—Scully, Scott, Murphy & Presser

[57] ABSTRACT

A system and method is presented for obtaining optical phase and amplitude measurements utilizing an acousto-optical modulator for modulating a laser light beam with a multifrequency electrical signal to form an image that is Fourier transformed and spatially distributed proportional to the frequency components of the electrical signal. An optical component such as a spatial light modulator is located in the Fourier plane and the modulated image is inversely transformed and optically heterodyned to produce a transformed image. The transformed image impinges a photodetector that produces an electrical output signal that is inputted to a network analyzer to measure phase and amplitude of the transformed image. The electrical output signal is compared with a reference signal and deviations from the reference signal provide a quantitative measurement of the phase and amplitude response of the spatial light modulator.

16 Claims, 2 Drawing Sheets

OPTICAL HETERODYNING SYSTEM AND METHOD FOR RAPID OPTICAL PHASE AND AMPLITUDE MEASUREMENTS

BACKGROUND OF THE INVENTION

This invention relates to the field of optical information processing and, more particularly, to amplitude and phase response measurements of an optical component.

Optical data processing systems have several advantages over electronic systems, such as, speed, dynamic range, resolution and reliability. Interest in such systems has increased recently due in part to the advances being made in the materials used to manufacture the optical components of the systems. For purposes of designing an optical data processing system, there is a need to determine quantitatively how an optical component modulates, in both amplitude and phase, a coherent beam of light transmitted or reflected by the optical component. In particular, there is a need to determine the amplitude and phase of a laser beam that has been modulated by a spatial light modulator (SLM) when it is used to convert an incoherent, "writing" light signal to a coherent, "reading" light pattern.

Amplitude characteristics are usually derived from relative intensity measurements, (for example, an "H-D" curve). Interferometric methods are used traditionally to observe the changes in phase of a coherent light beam when the beam is reflected or transmitted through an optical component. When using an interferometric system, phase changes are observed as light-to-dark fringe patterns which are due to constructive and destructive interference of the combined light beams. These methods are well known to those skilled in the field of optics.

The use of any one of several conventional interferometric methods to measure quantitatively the phase of an optical component is very time consuming and tedious even if automated. Furthermore, the phase must be calculated from the light intensity measurements of the fringe pattern maximum and minimum levels within the pattern itself. If S= measured value of light intensity, $S_{MAX}$, $S_{MIN}$= maximum and minimum values of S, and $\phi$=optical phase, then, $$S = \frac{(S_{MAX} + S_{MIN})}{2} + \frac{(S_{MAX} - S_{MIN})}{2} \sine\phi$$

$\phi$ is calculated from measured values of S, $S_{MAX}$ and $S_{MIN}$.

To map the phase and amplitude across the face of the optical component, a detector with a small aperture moving transverse to the output beam can be used. This is obviously a slow process when relatively large areas are to be evaluated. There is an additional complication when testing an SLM. Since the amplitude and phase response of an SLM will change with changes in the input, "writing", light intensity, a conventional interferometric method to measure phase $\phi$ would be very impractical to use. It is important to note that in this application, the amplitude response will alter the values of $S_{MAX}$ and $S_{MIN}$ so that these quantities must be determined for each input "write" light level used.

SUMMARY OF THE INVENTION

The present invention is directed to a system and method for obtaining real time phase and amplitude measurements of large area objects such as precision machine parts, electronic and optical components which can include spatial light modulators or wafer substrates as used in VLSI circuits by transmission and reflective architectures. The system utilizes an acousto-optic modulator (AOM) as a means for probing the test specimen with a laser beam that is modulated by a multifrequency electrical signal. The AOM operating in the Bragg regime, responds to the electrical signal by modulating the incident light beam, diffracting the beam into separate pencil beams, one for every component frequency of the electrical signal consistent with the time bandwidth of the AOM, and deflecting each of these pencils in proportion to its frequency. A lens focuses the beams onto a spatial frequency plane where each beam's position represents its frequency. Thus, the electrical signal frequency is proportional to the horizontal or x-position in the spatial frequency plane. Therefore, as the electrical signal is scanned through a plurality of frequencies, the laser beam is proportionally displaced in the x direction of the spatial frequency plane. The lens can be any lens suitable for Fourier transformation to provide the frequency distribution at the Fourier plane.

The component to be tested is positioned in the Fourier plane and can be scanned in the x direction in as little time as a few microseconds. The beams exiting the component by transmission or reflection are then inverse Fourier transformed and down converted or heterodyned at a photodetector which produces an electrical output signal. The down converting of the transformed image may be accomplished by combining the modulated image with a local oscillator light beam. The output signal is then inputted to a network analyzer that determines the amplitude and phase measurements of the signal. These measurements are compared with reference measurements stored in the network analyzer and a difference signal determines quantitatively the amplitude and phase modulation of the test optical component. Typically, reference signals are produced by operating the system without a test specimen or with some ideal specimen so that the electrical output signal is proportional to the amplitude and phase measurements of the light beams exiting the AOM.

The entire area of the test specimen can be probed for phase and amplitude response by displacing the optical component in the y direction. This can be accomplished by any scanning pattern such as a line or raster pattern, rectangular, circular, etc. Scanning in the y direction may also be achieved by other means such as by an orthogonal AOM scanner, piezoelectric scanner, galvanometer scanner or other means.

In addition, a reference plate can be inserted between the test specimen and the AOM to obtain a normalized response for subsequent data. The reference plate may be an optical flat or mirror or any other suitable element. The normalized reference data allows precise phase and amplitude measurements to be obtained. Furthermore, both reflective and refractive test specimens can be tested with equal facility by merely positioning the detection optics with respect to the frequency plane so that the inverse Fourier lens, the photodetector and local oscillator are situated to interact with light reflected from the optical component as opposed to being refracted thereby. Examples of components that may be tested in the present system include, optical flats, mirrors, lenses, passive and active optical elements, integrated circuits, thin films, microscope specimens, material roughness by profile imagery, gases, liquids and solids.

DETAILED DESCRIPTION OF THE INVENTION

Figure 1:
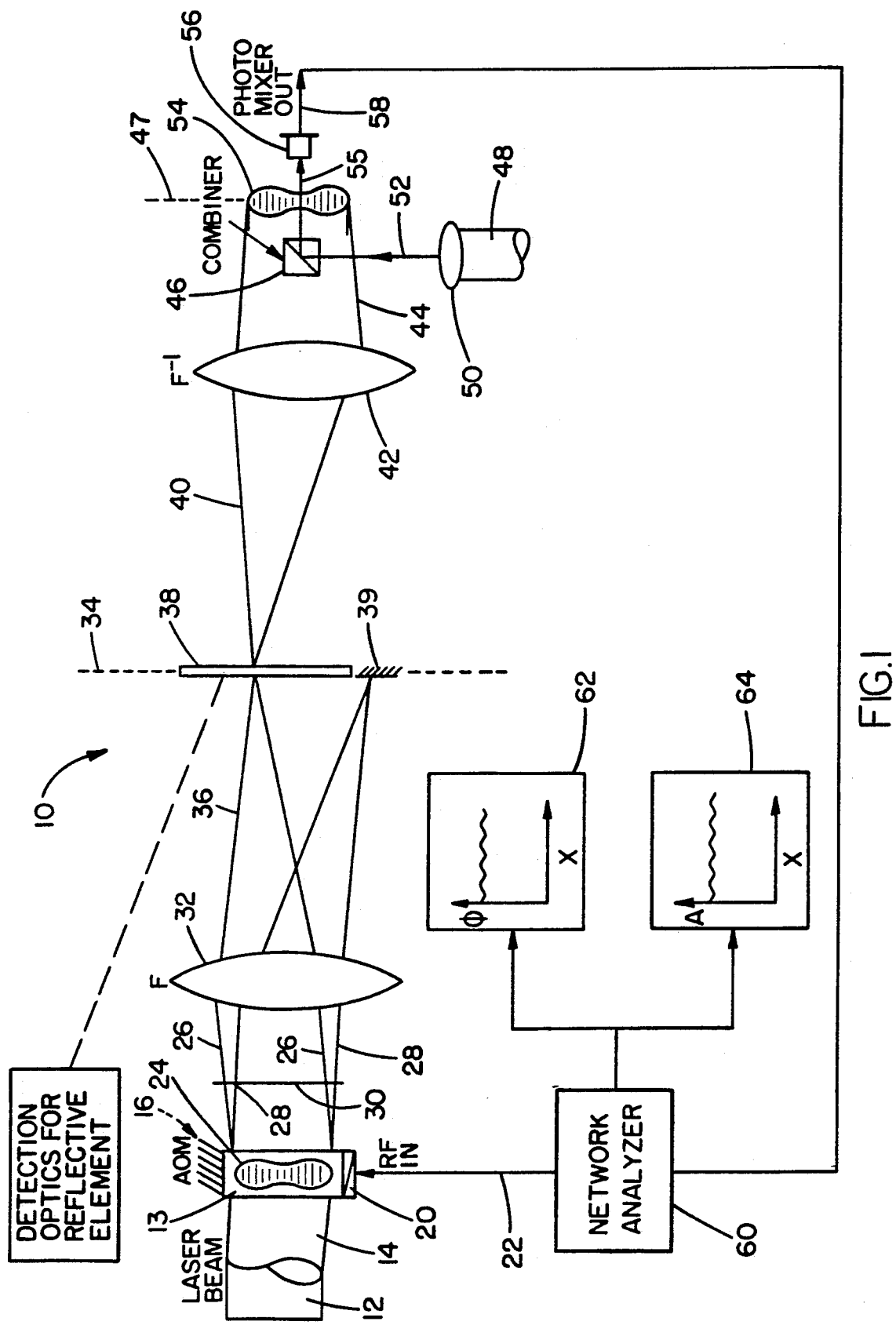
FIG. 1 is a schematic diagram of the optical heterodyning system of the present invention.

Referring now to FIG. 1, the optical heterodyning system 10 of the present invention comprises a light source 12, such as a laser, producing a beam 14 of radiation which is directed through a modulating means 16. The radiation source 12 can be a helium-neon gas laser, a laser diode (LED), or any other appropriate source producing a beam 14 of collimated, substantially coherent radiation.

The modulating means 16 impresses spectral and/or temporal signal intelligence on the radiation beam passing therethrough. Modulating means 16 may be an acoustooptic modulator (AOM) such as a Bragg Cell or the like. The Bragg Cell comprises a piezoelectric transducer 20 for converting an electric signal into an acoustic wave and an acoustooptic medium 18 such as a crystal. An electrical input signal, shown in FIG. 1 as RF signal 22, is converted to an acoustic wave by the piezoelectric transducer 20 acting on the medium 18. The acoustic wave thus launched in the medium 18 forms the acoustic field 24 which modulates the radiation beam 14 diffracting the beam for every component frequency of the RF signal 22 with the deflection of each beam proportional to its frequency.

It is well known that light passing through a Bragg Cell will be diffracted into a first order output beam and a zero order output beam. The first order output beam is defined by lines 26—26 and the zero order beam is defined by lines 28—28. The AOM imposes a narrowband phase modulation on the radiation beam 26. The beam may be corrected for suitable polarization by a reference plate 30 to obtain a normalized response for subsequent data. The reference plate 30 may be an optical flat or mirror or any other suitable element. The beam 26 is Fourier transformed by a Fourier transform lens 32 which produces a spatial frequency distribution at a frequency or Fourier plane 34. The spectrum of the RF signal is spatially distributed one dimensionally in the x direction. This light pattern signal contains a one for one spatial and temporal correspondence with the RF frequency distribution. The RF signal 22 is a linearly changing RF frequency signal so that as the RF signal 22 is scanned through the frequencies, the Fourier transformed beam 36 is proportionally displaced in the x direction. The Fourier transformed beam 36 is basically a scanning coherent beam in the Fourier plane.

The test specimen or optical component 38 to be tested is positioned at the frequency plane 34 and modulates the spatially distributed frequency components of the image. A zero order stop 39 is also located at the frequency plane to block the zero order beam. The modulated beam 40 exiting the component 38 is inverse Fourier transformed by inverse lens 42 to produce a modulated transformed image beam 44. The beam 44 forms an optical image 54 of the acoustic field 24 as modulated by the specimen 38 at an image plane 47.

The image beam 44 is combined with a local oscillator beam 52 by combiner 46 which may be a dielectric or conventional semisilvered mirror. A laser local oscillator beam 48 is focused by lens 50 to form the input beam 52 which is summed with image 54 to form beam 55 on an intensity sensitive square law photodetector 56 to achieve optical heterodyning or down conversion thus transforming the image beam 54 to an electrical output signal 58. The electrical output signal 58 is then inputted to a network analyzer 60 which measures the optical phase and amplitude of the image 54. Examples of the phase and amplitude measurements are schematically shown at 62, 64. The network analyzer 60 may also produce the RF signal 22 that drives the system.

To determine the modulation response of a particular component 38, the network analyzer compares the phase and amplitude measurements with a reference signal stored in the analyzer and any deviation from the stored reference signal provides a quantitative measure of the phase and amplitude response of the test optical component. The reference signal may be stored in the network analyzer by driving the system without a test specimen located at the Fourier plane. In the alternative, the reference signal or reference transformed image may be stored in the network analyzer by driving the system with an ideal test specimen or ideal optical component located at the Fourier plane.

The system of the invention avoids the problems with the prior art systems in measuring the amplitude and phase response of an optical component. If a beam of light traverses a region of thickness D with an index of refraction N, the optical phase of the exiting beam with respect to the entrance beam phase is $$\phi = \pi N D / \lambda \qquad (1)$$

where $\lambda$ = wavelength of light. Let $\omega_L$ represent the light angular frequency. The optical field of the output beam is $$E \sim \exp[j(\omega_L t + \phi)] \qquad (2)$$

If the light frequency is modulated with an acoustooptic modulator at a single frequency $\omega_M$ then $$E \sim \exp[j(\omega_L t + \phi_M t + \phi)] \qquad (3)$$

Square law down conversion of (3) with a local oscillator whose optical field varies as $$E_{L.O.} \sim \exp[j(\omega_L t] \qquad (4)$$

yields $$E \sim \exp[j(\omega_M t + \phi)] \qquad (5)$$

where the phase $\phi$ of the optical field now appears in the down convertion modulation signal.

Since $\phi$ is a function of x,y-position, the test specimen must be scanned in both x- and y-directions. Scanning in the x direction is accomplished by changing $\omega_M$ in the system configuration. Scanning in the y direction can be achieved by other means, such as, mechanically by moving mirrors, acousto optically with an orthogonal AOM, or electro-optically with an electro-optic unit.

The relationship between optical and electrical phase is developed below where it is shown that an optical phase disturbance will cause an equal phase disturbance in the RF output signals from the system.

The beam 26 is Fourier transformed by lens 32 and appears in the Fourier plane as $$f(t, x_1) \to F(\omega_1, x) \quad (6)$$

If a phase shift of $\omega_L t_o$ is added in the Fourier plane, by the shifting theorem, the inverse transform plane will experience a corresponding time delay of $t_o$, i.e., $$F(\omega_1, x)e^{j\omega L t_o} \to f(t - t_o, x_1) \quad (7)$$

Functionally, if the input signal is $$f(t, x_1) = K_1 \sin\left[\omega\left(t - \frac{x_1}{v}\right)\right] \quad (8)$$

then the output is $$f(t - t_o, x_1) = K_2 \sin\left(\omega t - \omega_L t_o - \omega \frac{x_1}{v}\right) \quad (9)$$

where $K_1$ and $K_2$ are constants.

This shows that the output is phase shifted by an angle $\omega_L t_o$.

This optical phase shift $\omega_L t_o$ is exactly equal to the corresponding electrical phase shift.

Figure 2:
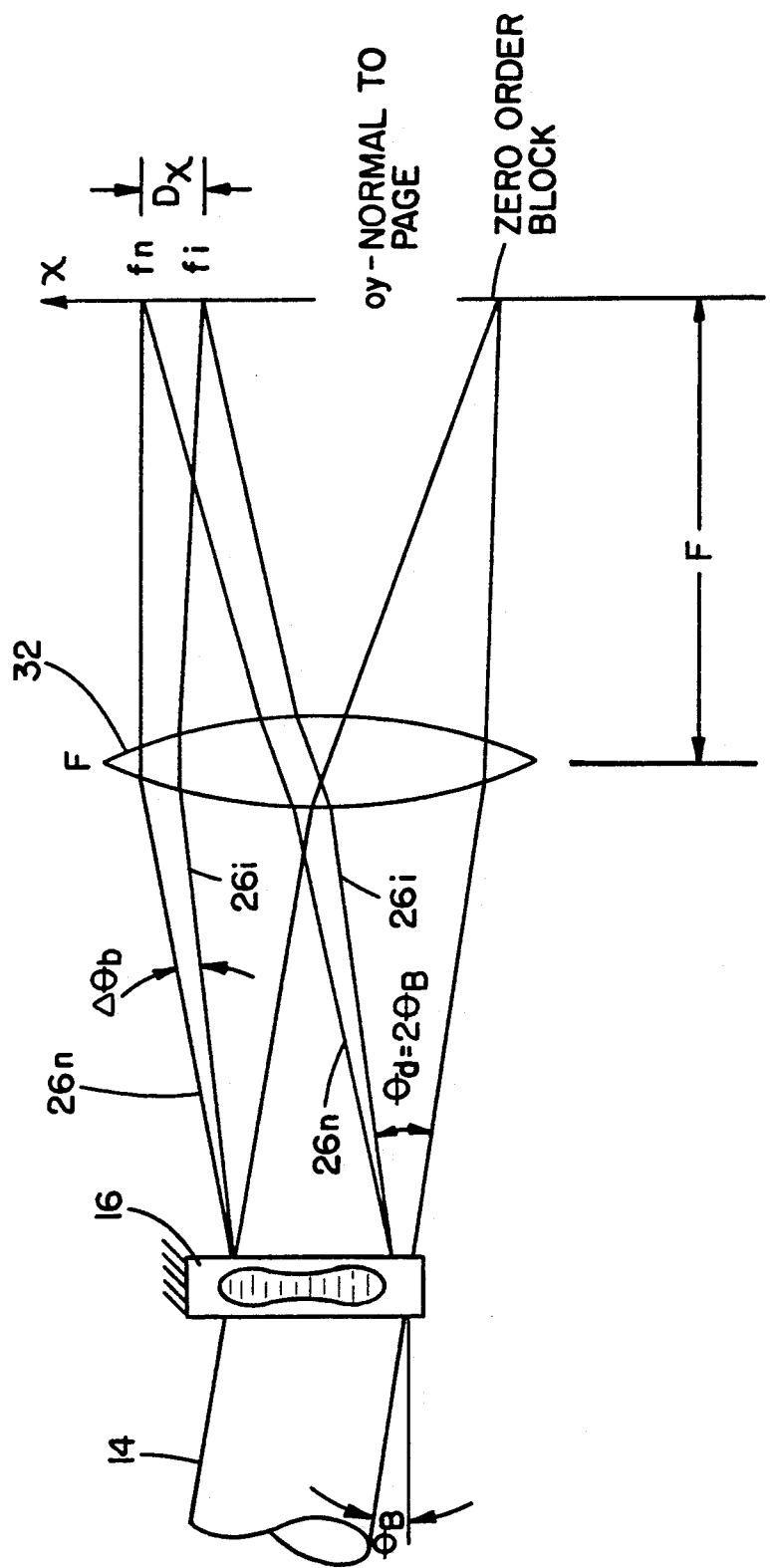
FIG. 2 is a schematic diagram of a portion of the system of FIG. 1 showing the displacement in the x direction caused by a change in the frequency of the electrical signal inputted to the AOM.

FIG. 2 relates the frequency (f) of the RF input to the Bragg diffraction in the Fourier plane. Here it is shown that the RF frequency (f) is directly proportional to the displacement in the x direction ($D_x$). The diagram in FIG. 2 shows the deflection for two RF frequencies, $f_n$ and $f_i$. The two RF frequencies result in two beams exiting the AOM 16. The beams are identified as $26_n$ and $26_i$. In FIG. 2, the x direction is the vertical direction and the y direction is normal to the page.

From the Bragg condition it is known that $\theta_d$, the angle of diffraction caused by the AOM is defined as $$\theta_d = \frac{f\lambda}{V} \quad (10)$$

where,
f = frequency of the RF signal,
$\lambda$ = wavelength of the laser
V = acoustic velocity of the AOM.

The change in the angle of diffraction, $\Delta\theta_d$ is defined as $$\Delta\theta_d = \frac{\Delta f \lambda}{V} \quad (11)$$

where, $$\Delta f = f_n - f_i.$$

The displacement of the position of the beam 26 at the frequency plane 34, $D_x$, is defined as:

$$D_x = F\Delta\theta_d \quad (12)$$

where,
F = focal length of lens 32.
From equations (10) and (11), $$D_x = \frac{\lambda(f_n - f)F}{V} \quad (13)$$

Thus, the RF frequency (f) is directly proportional to the displacement in the x direction.

The present invention provides a system and method for obtaining real time phase and amplitude measurements of large area test specimens such as IC wafers and spatial light modulators. The system utilizes an acousto optic modulator that modulates a laser with a multifrequency RF signal and a Fourier lens to produce a spatial distribution of the laser beam proportional to the frequency components of the RF signal, so that as the RF signal is scanned through the range of frequencies, the laser beam is proportionally displaced in the x direction of the Fourier plane. The SLM is located at the Fourier plane and can thus be scanned in the x direction by the changing frequency of the RF signal and in the y direction by mechanical or optical means. The exiting laser beam is then inverse Fourier transformed and heterodyned at a photodetector to produce an electrical output signal. A network analyzer measures the phase and amplitude of the SLM modulated light beam from the electrical output signal. The output signal is compared with a stored reference signal in the network analyzer and any deviation from the stored reference signal provides a quantitative measure of the phase and amplitude response of the SLM.

While the invention has been particularly shown and described with respect to the preferred embodiments thereof, it should be understood by those skilled in the art that the foregoing and other changes in form and details may be made therein without departing from the spirit and scope of the invention which should be limited only by the scope of the appended claims.

What is claimed is:

1. A system for obtaining optical phase and amplitude measurements comprising:
   means for modulating a coherent light beam with a multifrequency electrical input signal to form an image;
   means for Fourier transforming said image to produce a scanning coherent light beam in the Fourier plane, said scanning coherent light beam interacts with an optical component located in the Fourier plane to form a modulated transformed image in the frequency plane;
   means for inverse Fourier transforming said modulated transformed image for detecting an electrical output signal therefrom from which amplitude and phase measurements of said modulated transformed image is determined; and
   analyzer means for determining said amplitude and phase measurements of said modulated transformed image from said electrical output signal and for storing said amplitude and phase measurements, said analyzer means compares said amplitude and phase measurements of said modulated transformed image to the amplitude and phase measurements of a reference transformed image to quantitatively measure the amplitude and phase of said optical component.

2. The system of claim 1 wherein the modulating means comprises an acousto-optical modulator having:
   a coherent optical input light beam signal interacting with an acoustic field generated by an electrically stimulated piezoelectric transducer; and
   an electrical input signal terminal connected to the piezoelectric transducer.

3. The system of claim 1 wherein the Fourier transforming means comprises
   a Fourier lens positioned rearwardly of the Fourier plane.

4. The system of claim 1 wherein the inverse Fourier transforming means comprises:

an inverse Fourier lens positioned rearwardly of the Fourier plane;

optical means for combining the modulated transformed image and a local oscillator light beam for down-converting the modulated transformed image; and a photodetector for changing the down converted modulated transformed image to the electrical output signal.

5. The system of claim 1 wherein said analyzer means is coupled to said modulating means for producing the multifrequency electrical input signal inputted to said modulating means.

6. A system for obtaining optical phase and amplitude measurements comprising:

means for modulating a coherent light beam with a multifrequency electrical input signal to form an image;

means for forming a Fourier plane and spatially distributing the frequency components of the image in the Fourier plane;

optical component means located at said Fourier plane for modulating the spatially distributed frequency components;

means for scanning the optical component means with the spatially distributed frequency components to produce a modulated image;

means for inversely Fourier transforming the modulated image;

means for combining the modulated image with a local oscillator light beam for down converting the modulated image;

photodetector means for changing the down converted modulated image to an electrical output signal; and analyzer means for measuring the optical phase and amplitude of the modulated image and for comparing said measurements to measurements of a reference image to determine the amount of phase and amplitude modulation of the optical component means.

7. The system of claim 6 wherein the modulating means comprises an acousto-optical modulator having:

a coherent optical input light beam signal interacting with an acoustic field generated by an electrically stimulated piezoelectric transducer; and an electrical input signal terminal connected to the piezoelectric transducer.

8. The system of claim 7 wherein the Fourier plane forming means comprises a Fourier lens positioned forwardly of the Fourier plane.

9. The system of claim 8 wherein the inversely Fourier transforming means comprises an inverse Fourier lens positioned rearwardly of the Fourier plane.

10. The system of claim 9 wherein the scanning means includes means for changing the frequencies of the multifrequency electrical signal to spatially distribute the frequency components in the x direction.

11. The system of claim 10 wherein the scanning means include means for changing the position of the x-directed scan in the y direction.

12. A method for obtaining optical phase and amplitude measurements comprising:

modulating a coherent light beam with a multifrequency electrical input signal to form an image;

Fourier transforming said image to produce a scanning coherent light beam in the Fourier plane, said scanning coherent light beam interacts with an optical component located in the Fourier plane to form a modulated transformed image in the frequency plane;

inverse Fourier transforming said modulated transformed image for detecting an electrical output signal therefrom which amplitude and phase measurements of said modulated transformed image is determined; and analyzing to determine said amplitude and phase measurements of said modulated transformed image from said electrical output signal and for storing said amplitude and phase measurements, said analyzing step compares said amplitude and phase measurements of said modulated transformed image to the amplitude and phase measurements of a referenced transformed image to quantitatively measure the amplitude and phase of said optical component.

13. The method of claim 12 where inverse Fourier transforming includes the steps of:

combining the modulated transformed image and a local oscillator light beam for down converting the modulated transformed image; and changing the down converted image to the electrical output signal.

14. A method for obtaining optical phase and amplitude measurements comprising:

modulating a coherent light beam with a multifrequency electrical input signal to form an image;

forming a Fourier plane and spatially distributing the frequency components of the image in the Fourier plane;

positioning an optical component means at said Fourier plane for modulating the spatially distributed frequency components;

scanning the optical component means with the spatially distributed frequency components to produce a modulated image;

inversely Fourier transforming the modulated image;

combining the modulated image with a local oscillator light beam for down converting the modulated image;

changing the down converted modulated image to an electrical output signal; and measuring the optical phase and amplitude of the modulated image and comparing said measurements to measurements of a reference image for determining the amount of phase and amplitude modulation of the optical component means.

15. The system of claim 14 wherein the scanning step includes changing the frequencies of the multifrequency electrical signal to spatially distribute the frequency components in the x direction.

16. The system of claim 15 wherein the scanning step include changing the position of the x-directed scan in the y direction.

* * * * *

UNITED STATES PATENT AND TRADEMARK OFFICE
CERTIFICATE OF CORRECTION

PATENT NO. : 5,008,851
DATED : April 16, 1991
INVENTOR(S) : Robert W. Brandstetter, et al.

It is certified that error appears in the above-identified patent and that said Letters Patent is hereby corrected as shown below:

Column 4, line 45: "$[j(\omega_L t + \phi_m t + \phi)]$" should read as $--[j(\omega_L t + \omega_M t + \phi)]--$ Column 5, line 40: "laser" should read as --laser beam 14,--

Signed and Sealed this

Sixth Day of October, 1992

Attest:

DOUGLAS B. COMER

Attesting Officer

Acting Commissioner of Patents and Trademarks